United States Patent [19]

Boguslawski et al.

[11] Patent Number: 4,689,294

[45] Date of Patent: Aug. 25, 1987

[54] ENHANCEMENT OF HYBRIDIZATION OF NUCLEIC ACIDS BY ANIONIC POLYMERS

[75] Inventors: Sophie J. Boguslawski, Elkhart, Ind.; Leslie H. DeRiemer Anderson, Encinitas, Calif.

[73] Assignee: Miles Laboratories, Inc., Elkhart, Ind.

[21] Appl. No.: 672,941

[22] Filed: Nov. 19, 1984

[51] Int. Cl.$^4$ .................... C12Q 1/68; C12N 15/00
[52] U.S. Cl. ........................................ 435/6; 935/78; 435/803; 435/810
[58] Field of Search .................... 525/54.1; 435/6, 803, 435/810; 436/501, 530, 808; 935/78

[56] References Cited

U.S. PATENT DOCUMENTS 4,302,204 11/1981 Wahl et al. ............... 436/501 X
4,358,535 11/1982 Falkow et al. ............. 435/35 X

OTHER PUBLICATIONS

*Chemical Abstracts*, vol. 94, No. 8, 1981, p. 8, Abstract No. 47875v, Inaki, Y., et al. "Functional Monomers . . . Nucleic Acid Bases".
*Chemical Abstracts*, vol. 99, No. 20, 1983, p. 99, Abstract No. 160350m, Lion Corp., "Liquid Detergents".
Martinell, J. et al. *Proc. Natl. Acad. Sci. USA*, vol. 78, No. 8, Aug. 1981, pp. 5056-5060.
Subirana, J. A. et al. *Biopolymers*, vol. 44, 1966, pp. 171-187.

*Primary Examiner*—Esther M. Keppinger
*Assistant Examiner*—Jeremy Jay
*Attorney, Agent, or Firm*—Andrew L. Klawitter

[57] ABSTRACT

The rate of hybridization between two complementary polynucleotide segments in an aqueous medium is increased by the presence of the anionic polymers polyacrylate and polymethacrylate. The acceleration effect is particularly useful in nucleic acid hybridization assays involving immobilization of sample nucleic acids and the use of labeled probes. Nonspecific binding of probe to nitrocellulose supports is substantially lower in the presence of the present polymers than in the presence of the prior art accelerator dextran sulfate. Polyacrylate is particularly advantageous since it has been found to be effective at low concentrations and is significantly less expensive than the prior art compound.

28 Claims, 5 Drawing Figures

ENHANCEMENT OF HYBRIDIZATION OF NUCLEIC ACIDS BY ANIONIC POLYMERS

FIELD OF THE INVENTION

This invention concerns the specific molecular binding, or hybridization as it is commonly known, of complementary polynucleotide segments. As such, the invention has particular application to nucleic acid hybridization methods and reagent systems for detecting specific polynucleotide sequences. The principle of nucleic acid hybridization assays was developed by workers in the recombinant DNA field as a means for determining and isolating particular polynucleotide base sequences of interest. It was found that single stranded nucleic acids, e.g., DNA and RNA, such as obtained by denaturing their double stranded forms, will hybridize or recombine under appropriate conditions with complementary single stranded nucleic acids. By labeling such complementary probe nucleic acids with some readily detectable chemical group, it was then made possible to detect the presence of any polynucleotide sequence of interest in a test medium containing sample nucleic acids in single stranded form.

In addition to the recombinant DNA field, the hybridization technique can be applied to the detection of polynucleotides of analytical importance in the fields of human and veterinary medicine, agriculture, and food science, among others. In particular, the technique can be used to detect and identify etiological agents such as bacteria and viruses, to screen bacteria for antibiotic resistance, to aid in the diagnosis of genetic disorders such as sickle cell anemia and thalassemia, and to detect cancerous cells. A general review of the technique and its present and future significance is provided in Biotechnology (August 1983), pp. 471–478.

INFORMATION DISCLOSURE

The following information is provided for the purpose of making known information believed by the applicants to be of possible relevance to the present invention. No admission is necessarily intended, nor should be construed, that any of the following information constitutes prior art against the present invention.

Wetmur (1974), Biopolymers 14:2517–2524, found that 10% dextran sulfate accelerates the hybridization rate of DNA in solution by about ten-fold. Dextran, a nonionic polymer, accelerated the hybridization rate to a much smaller extent. There was a linear relationship between the logarithm of the hybridization rate and the viscosity of the polymer solution. Wahl et al (1970), Proc. Natl. Acad. Sci. 76:3683–3687, covalently immobilized single stranded DNA on diazobenzyloxymethylcellulose and reported that the hybridization with radiolabeled DNA in solution was accelerated as much as 100-fold by 10% dextran sulfate. The use of dextran sulfate and other charged polysaccharides to accelerate hybridization reactions in which one of the polynucleotides is covalently attached to a solid phase is described in U.S. Pat. No. 4,302,204. Ten percent dextran sulfate is frequently used in hybridization reactions where very low quantities of a DNA sequence need to be detected.

Hybridization reactions can require long incubation periods and any means for shortening the incubation can be useful in many practical applications of the assay method. However, the use of dextran sulfate to accelerate hybridization has shortcomings. The polymer is relatively expensive and is used in large quantities especially when a large area of support material needs to be covered by hybridization solution such as for Southern blots. Furthermore, 10% dextran sulfate increases the nonspecific binding of labeled DNA probes to nitrocellulose and cellulose supports as reported by Wahl et al, supra, and Ranki et al (1983), Current Topics in Microbiology and Immunology 104:307–318.

Polyethylene glycol was found by Renz and Kurz (1984), Nucleic Acids Research 12:3435–3444, to be superior to dextran sulfate for hybridization with peroxidase labeled nucleic acids. However, polyacrylate has been specifically reported not to affect the rate of hybridization of DNA—Subirana and Doty (1966), Biopolymers 4:171–187.

SUMMARY OF THE INVENTION

It has now been found that the anionic acrylate polymers increase the rate of hybridization between complementary polynucleotide segments in an aqueous medium. Furthermore, these new accelerator compounds have particular advantages over the most commonly used prior art compound dextran sulfate. The present polymers achieve the same enhancement of hybridization rate as dextran sulfate and are resistant to microbial degradation.

The acceleration effect is particularly useful in nucleic acid hybridization assays including solution assays and solid-phase assays such as involving immobilization of sample nucleic acids and the use of labeled probes. Nonspecific binding of probe to the commonly used nitrocellulose supports is substantially lower in the presence of polyacrylate and polymethacrylate than in the presence of dextran sulfate. Polyacrylate is particularly advantageous due to the finding that it is effective at low concentrations and is significantly less expensive than the prior art compound.

Figure 1:
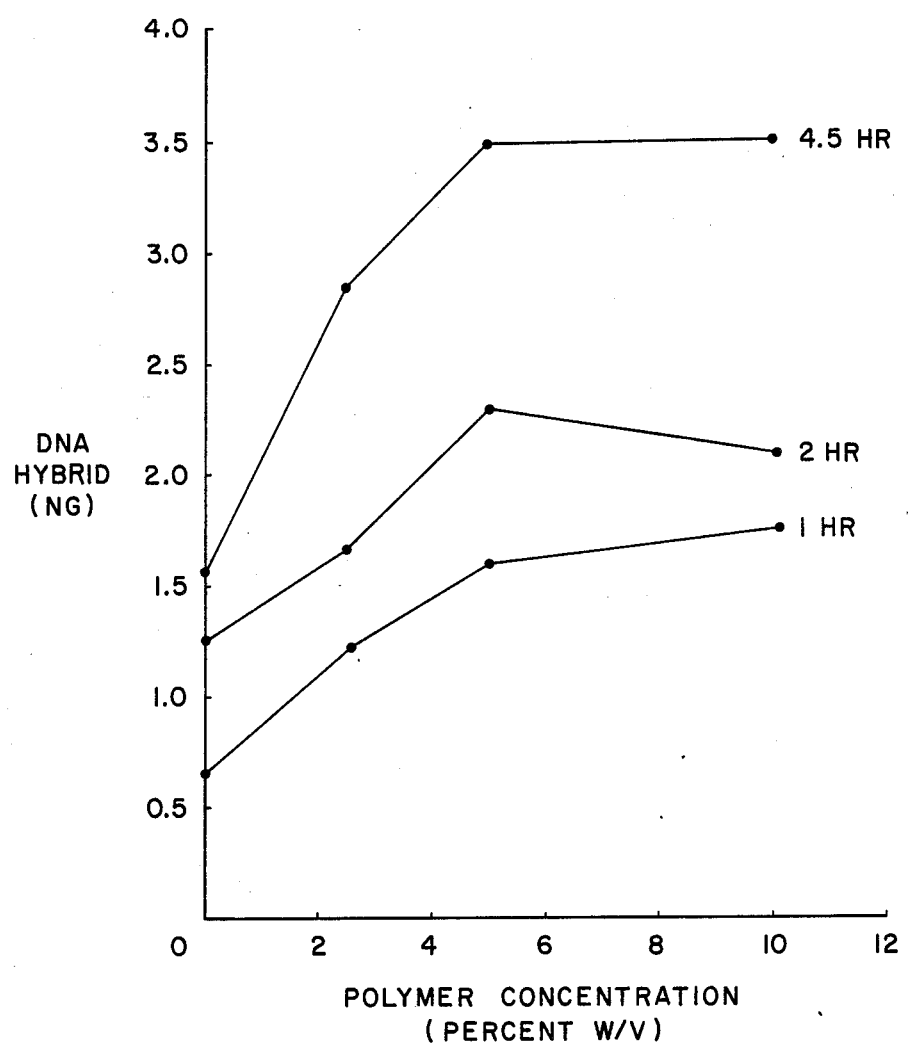
FIGS. 1–3 are graphs showing the effect of the concentration of polyacrylate and polymethacrylate compared to dextran sulfate on hybridization rate.

Details of the experiments from which the data presented in the graphs were obtained are given in the Examples below.

DESCRIPTION OF THE PREFERRED EMBODIMENTS

Polyacrylate and polymethacrylate will be present in the aqueous hybridization medium in their anionic form which can be formed in situ or by addition of the polymers in any of their available salt forms, e.g., sodium, potassium, ammonium. In choosing a salt, one will consider the effect of the particular countercation on the other components of the hybridization medium. For example, one would tend not to select the potassium salt when a dodecylsulfate surfactant is to be present to guard against possible precipitation. The hybridization medium will be aqueous and can contain various constituents in addition to the present polymers as are conventionally known including buffers, organic solvents, surfactants, nonspecific nucleic acids, and other polymers such as Ficoll (a copolymer of sucrose and epichlorohydrin available from Pharmacia Fine Chemicals, Piscataway, N.J.) and polyvinylpyrrolidone. The concentration of the present polymers in the hybridization medium, expressed in units of percent weight to volume (w/v), will normally be between about 0.2% and 10%, preferably between about 0.5% and 5%, for polyacrylate, and normally between about 1.0% and 50%, and preferably between about 5% and 25%, for polymethacrylate. The molecular weight of the polymers can vary widely. Normally, the molecular weight will be between about 5,000 and 1,000,000 daltons, and preferably between about 50,000 and 500,000 daltons.

The anionic acrylate polymers polyacrylate and polymethacrylate have been found to be particularly advantageous as accelerators of nucleic acid hybridization. It will be evident in the art that various equivalent acrylate polymers can be used for this purpose without departing from the spirit and scope of the present invention. Variously substituted acrylate homopolymers and copolymers are contemplated to have the acceleration properties of the present compounds and will be considered as equivalents for the purposes of the claims hereof.

The present invention is useful whenever it is desired to enhance the rate of hybridization of two complementary polynucleotide segments in an aqueous medium. Such segments will normally comprise part or the whole of distinct polynucleotide strands. The term polynucleotide as used herein includes those shorter length strands sometimes referred to as oligonucleotides and includes RNA, DNA, and suitable derivatives thereof. The formation of DNA/DNA, RNA/RNA, as well as mixed RNA/DNA hybrids will be accelerated in aqueous media containing the present polymers.

The principal application of the acceleration effect is in nucleic acid hybridization assays. The use of the present polymers is not limited to any particular hybridization format, but may be more desirable and advantageous in certain formats. In general, however, the manner in which hybridization is carried out is a mere matter of choice and convenience. Currently known hybridization formats and improvements made in the future will be applicable to the present invention.

In general, hybridization methods comprise the steps of (a) forming an aqueous assay medium comprising single stranded sample nucleic acids and a polynucleotide probe having a base sequence substantially complementary to the sequence to be determined, and (b) determining the formation of hybridized probe. Depending on the particular assay format involved, the sample nucleic acids can be immobilized prior to formation of the assay medium with the probe, the probe can be labeled, the probe can be immobilized, and/or the sample and probe nucleic acids can both be in solution.

Conventional hybridization formats which are particularly useful include those wherein the sample nucleic acids or the polynucleotide probe is immobilized on a solid support (solid-phase hybridization) and those wherein the polynucleotide species are all in solution (solution hybridization).

A. Solid-phase Hybridization

In this approach, one of the polynucleotide species participating in hybridization is fixed in an appropriate manner in its single stranded form to a solid support. Useful solid supports are well known in the art and include those which bind nucleic acids either covalently or noncovalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted, in a single stranded, labeled form, with the support. Appropriate labels are available by which to detect resulting hybridization on the support. Typically, a solid-phase hybridization technique will proceed as follows:

(1) the test sample is subjected to conditions to release and denature nucleic acids and resulting single stranded nucleic acids are immobilized on a solid support, e.g., a liquid sample such as a body fluid is applied to a nitrocellulose membrane, the deposited cells are lysed and released DNA denatured, and the membrane is baked in vacuo at 80° C. for 2 hours to fix single stranded DNA to the membrane; alternatively, the cells are first lysed and released DNA is denatured and then applied to the nitrocellulose membrane;

(2) the support is contacted with the labeled probe in excess under favorable hybridization conditions, e.g., after saturating all nonspecific DNA binding sites on the membrane by treatment at 40°-60° C. with a prehybridization solution comprising buffer (e.g., 2XSSC), protein such as bovine serum albumin, Ficoll, polyvinylpyrrolidone, a denatured foreign DNA such as from calf thymus or salmon sperm, and a polymer of the present invention; typically the hybridization conditions will be the same as the prehybridization conditions except the time of incubation will usually be longer;

(3) removing labeled probe which has not hybridized to the immobilized single stranded nucleic acid, e.g., by simple washing of the membrane; and (4) measuring the label on the support in accordance with the detectable characteristic of the label.

The present invention is particularly advantageous for solid-phase hybridization methods involving immobilization of sample nucleic acid on a solid support since the acceleration effect is most evident in situations where relatively low nucleic acid amounts are immobilized and excess probe is brought into contact with the immobile phase in the aqueous hybridization medium.

Traditionally, the label will comprise a radioisotope such as $^{32}P$ and will be detected by scintillation counting or autoradiography, however, as will be more fully described below, nonradioisotopic detection schemes can also be used.

Additional steps can also be included in the above typical protocol. For example, where particularly short DNA fragments (e.g., less than about 100 bases) or RNAs are to be immobilized, such polynucleotides can be first derivatized with glyoxal and then applied to the support. Alternatively, reactive cellulose can be used to covalently bind the polynucleotides, usually after an initial purification of the sample to isolate nucleic acids according to standard methods.

Instead of immobilizing sample nucleic acids and using labeled probe, it is also possible to label sample nucleic acids in situ by known methods and thereafter add the probe in immobilized form. The end measurement is the same, detection of the label associated with the support. A format of this type that is of particular interest detects RNA or DNA sequences using an immobilized RNA probe and an antibody, or a fragment thereof, preferably labeled, that binds to RNA/RNA or RNA/DNA hybrids specifically. This format is described in detail in commonly assigned U.S. patent application Ser. No. 616,132, filed June 1, 1984 and now abandoned.

Another method of interest is the sandwich hybridization technique wherein one of two mutually exclusive fragments of the homologous sequence of the probe is immobilized and the other is labeled. The presence of bacterial nucleic acids results in dual hybridization to the immobilized and labeled probe segments, again with the same ultimate measurement of support-associated label. See Methods in Enzymology 65:468(1980) and Gene 21:77-85 (1983) for further details.

B. Solution Hybridization

The present method can also be used for detection of bacterial nucleic acids in a solution format. This normally requires that the homologous sequence be in single stranded form, be it RNA or DNA. This will be referred to as the probe polynucleotide.

In a solution format, the specimen nucleic acids are first released if necessary from cells in the sample by lysis, and then denatured. These steps can be combined by heating the sample to 100° C. or by exposing it to base. After adding a solution containing a large excess of the probe, hybridization is allowed to occur under conditions of ionic strength and temperature empirically determined to give the desired probe specificity and sensitivity.

Hybrids can be detected and quantitated using a number of methods. For example, after hybridization the remaining single stranded nucleic acid can be hydrolyzed into small fragments with the single-strand specific nuclease $S_1$. Acid precipitation followed by centrifugation or filtration can be used to concentrate the hybrids and separate them from the hydrolyzed single-stranded polynucleotides. The amount of precipitate collected is then quantitated. In another approach, hybridized and single-stranded polynucleotides can be separated by chromatography on hydroxyapatite. Where the probe is labeled and provides a signal that is measurably different when the probe is hybridized compared to when unhybridized, separation steps can be avoided. See published European Patent Appl. No. 70,685.

Another method of interest which can be practiced in both solid-phase and solution formats involves detection of hybrids by binding of antibody, or a fragment thereof, preferably labeled, to intercalation complexes as described in commonly assigned U.S. patent application Ser. No. 560,429, filed Dec. 12, 1983.

Various labels are used in hybridization methods benefiting from the present invention. Radioisotopic labels include $^3H$, $^{35}S$, $^{32}P$, $^{125}I$, and $^{14}C$. Nonradioisotopic materials can also be used as labels and include, but are not limited to, haptens or other ligands, fluorescers, chemiluminescers, chromophores, and participants in enzymic reactions, such as enzymes, enzyme cofactors, enzyme substrates, and enzyme inhibitors.

The present invention additionally provides a reagent system, i.e., reagent combination or means, comprising all of the essential elements required to conduct a desired assay method. The reagent system is presented in a commercially packaged form, as a composition or admixture where the compatibility of the reagents will allow, in a test device configuration, or as a test kit, i.e., a packaged combination of one or more containers, devices, or the like holding the necessary reagents, and usually including written instructions for the performance of assays. Reagent systems of the present invention include all configurations and compositions for performing the various hybridization formats described herein and will comprise at least the probe and a polymer of the present invention. Particularly preferred is a test kit for performing a solid-phase hybridization protocol comprising (1) a solid support capable of immobilizing single stranded nucleic acid resulting from treatment of a test sample to release and denature bacterial nucleic acids, (2) a labeled polynucleotide probe selected from the various types described herein and (3) a polymer of the present invention. Preferably, such kit will additionally comprise foreign nucleic acid for use in substantially saturating nucleic acid adsorption sites on the support after immobilization of sample nucleic acid, along with, optionally, other desired ingredients for a prehybridization solution. Also, the kit will preferably include a chemical lysing and denaturing agent, e.g., alkali, for treating the sample to release single stranded nucleic acid therefrom. Ingredients for the hybridization reaction, if different from the prehybridization solution, will also be preferably included in the kit. The reagent system can, of course, include other materials and solutions as are known in the art and which may be desirable from a commercial and user standpoint, such as buffers, diluents, standards, and so forth.

The present invention will now be illustrated, but is not intended to be limited, by the following examples.

EXAMPLES

Materials and Methods

A. Preparation of $^{35}S$ - Labeled DNA Probes

Hind III fragments of λ DNA (New England BioLabs; Beverly, Mass.) were radioactively labeled by nick-translation essentially as described by Rigby et al (1977), J. Mol. Biol. 113:237–251, except that deoxyadenosine 5'-[α-thio-$^{35}S$]triphosphate (~1000–1500 Ci/mmol, New England Nuclear; Boston, Mass.) was used instead of [α-$^{32}P$]dATP and the reaction was incubated for three hours. Labeled DNA was separated from free nucleotides by chromatography on NACS-52 TM resin (Bethesda Research Laboratories; Gaithersburg, Md.) as recommended by the manufacturer. It was then precipitated with ethanol, dissolved in TE buffer (10 mM Tris-HCl, pH 7.2, 1 mm EDTA) containing 10 millimolar (mM) dithiothreitol(DTT) and stored at −20° C. The DNA concentration was determined by a fluorescent assay with ethidium bromide as described by Morgan et al (1979), Nucleic Acids Res. 7:547–569. Nick-translated preparations had specific activities from $5 \times 10^6$ to $4.8 \times 10^7$ counts per minute per microgram (cpm/μg) and were diluted with unlabeled Hind III digest of λ DNA to obtain the probes of required specific activity.

The sizes of the nick-translated Hind III digested λ DNA, determined by electrophoresis on a denaturing alkaline 1% agarose gel, were as follows: less than 6% was larger than 6600 base pairs (bp), 42% was between 6600 and 2000 bp, 33% was between 2000 and 560 bp, and 20% was below 560 bp.

B. Immobilization of DNA on Nitrocellulose Membrane

Nitrocellulose membranes (BA85 sheets, Schleicher and Schuell; Keene, N.H.) were soaked in water for at least 15 minutes and mounted on Minifold filtration apparatus (Schleicher and Schuell). One-half milliliter of 15×SSPE (1×SSPE =0.18M NaCl, 10 mM sodium phosphate buffer, pH 7.7, 1 mM EDTA) was washed through each well. Heat denatured Hind III fragments of λ DNA and carrier DNA (salmon sperm DNA) were diluted into 15×SSPE, and 200 microliter (μL) aliquots containing indicated levels of λ-Hind III DNA and 5 μg carrier DNA were applied to each well. Control wells for measurement of nonspecific binding of labeled probe to nitrocellulose were prepared with 5 μg of carrier DNA only. The wells were washed with 250 μL of 15×SSPE and the membrane was air-dried and baked at 80° C. in a vacuum oven for two hours. Circles of 0.28 cm$^2$ encompassed by the wells were cut out and stored at room temperature in a desiccator until used.

C. Preparation of Polymer Stock Solutions

Polymer stock solutions were prepared in water on weight/volume basis at the following concentrations: dextran sulfate, sodium salt, (~500,000 molecular weight, Sigma Chemical Co.; St. Louis, Mo.) as 20% solution; poly(methacrylic acid) (undefined molecular weight, Polysciences; Warrington, Pa.) as 40% solution neutralized with 5 N NaOH; poly(acrylic acid) (~90,000, ~300,000, ~450,000 molecular weight, Polysciences) as 10% solutions neutralized with 10 N NaOH.

D. Hybridization Reactions

Hybridization reactions were carried out in tightly stoppered polystyrene tubes (10×50 mm). The nitrocellulose disks with bound DNA were presoaked briefly in 6×SSPE and placed in the tubes. Sixty microliters of prehybridization solution was added composed of 6×SSPE, 5×Denhardt solution (1×Denhardt was 0.02% Ficoll, 0.02% polyvinylpyrrolidone and 0.02% bovine serum albumin), 0.5% sodium dodecylsulfate, 100 micrograms per milliliter (μg/mL) denatured salmon sperm DNA, and polymer as indicated. The tubes were incubated at 65° C. overnight. Hybridization reactions were initiated by adding 10 μL of $^{35}$S-labeled probe of indicated specific activity which was heat denatured and then made 70 mM in DTT. The reaction mixtures were incubated at 65° C. for indicated periods and then the nitrocellulose disks were washed with 0.75 mL portions of 2×SSPE, 0.1% sodium dodecylsulfate as follows: three washes for five minutes at room temperature; two washes for ten minutes at 65° C. and two washes five minutes each at room temperature. The disks were drained well, dried and bound $^{35}$S was measured. Each data point is an average of results from triplicate disks and is corrected for nonspecific binding of labeled DNA to control disks.

Results

A. Effects of Polymer Concentrations on Hybridization Rate

Figure 2:
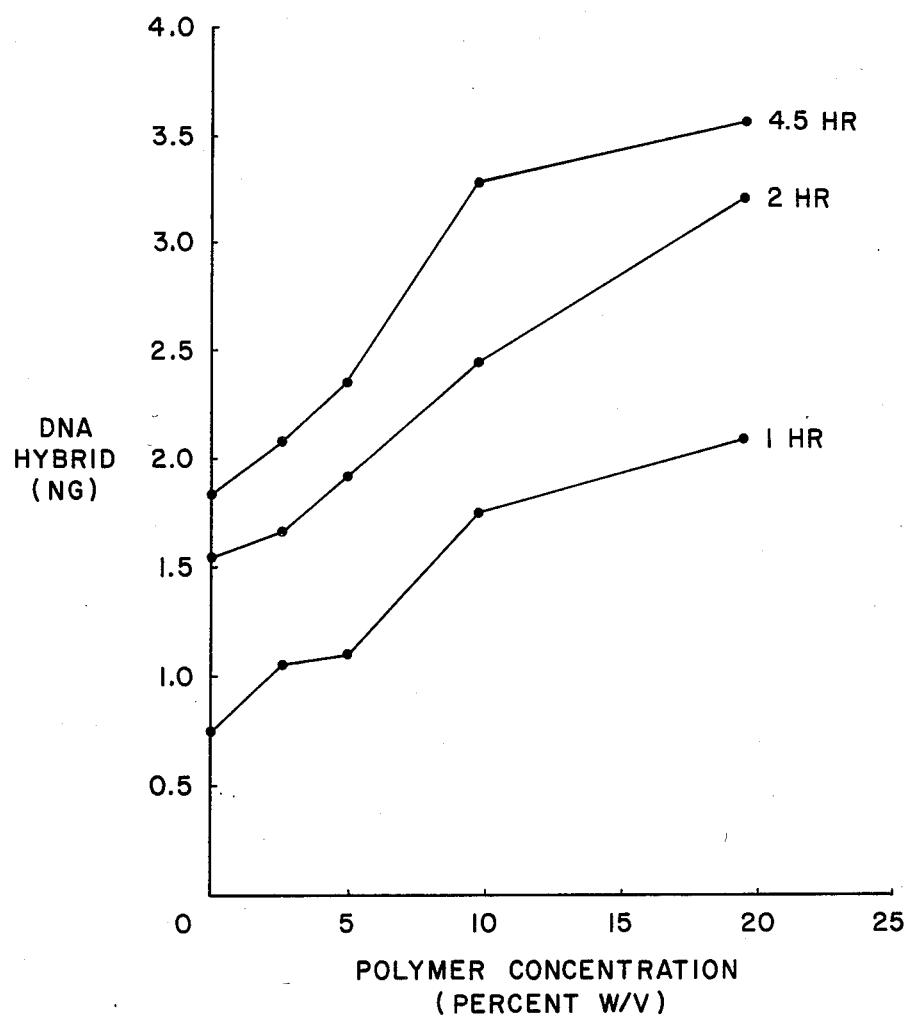
Figure 3:
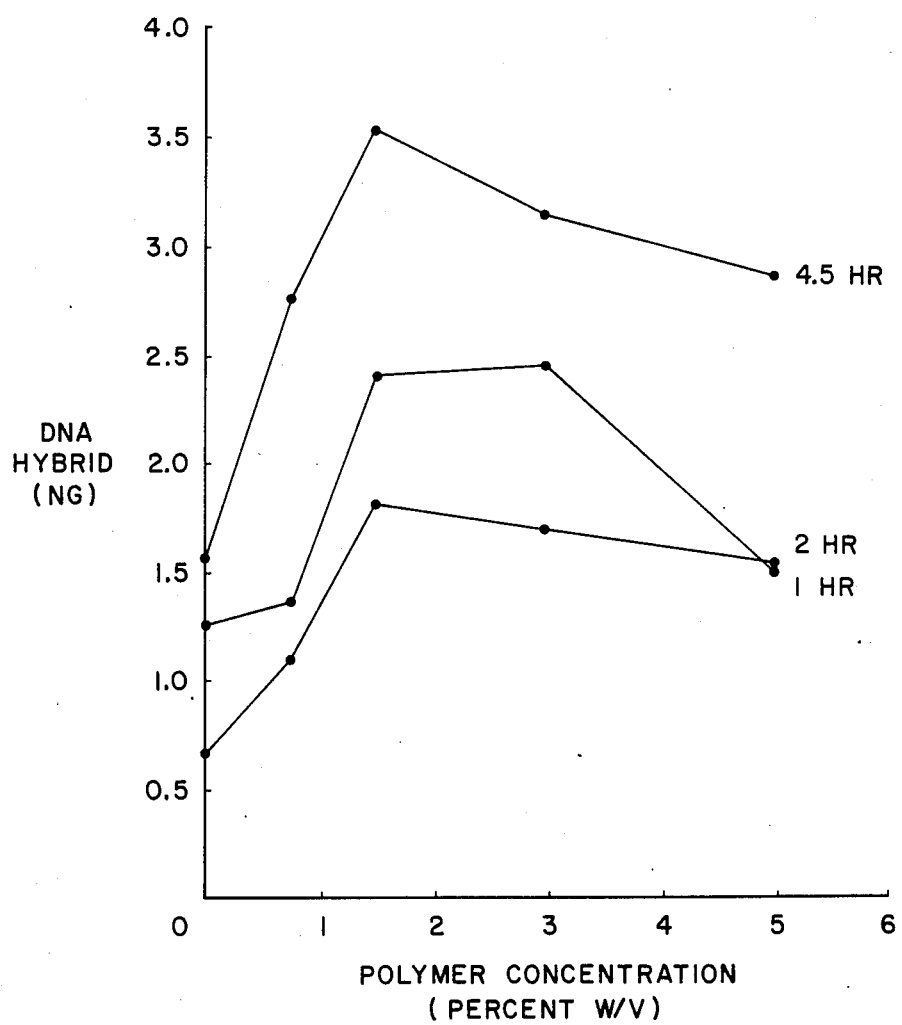

Initial hybridization rates were measured with various concentrations of each polymer. Each nitrocellulose filter had 5 nanograms (ng) of immobilized Hind III digest of λ DNA. It was hybridized with 0.1 μg of $^{35}$S-DNA (4.5×10$^6$ cpm/μg). The results in FIG. 1 show that the hybridization rate increased with dextran sulfate concentration up to 5%. In some experiments a small additional increase was observed with 10% dextran sulfate which is the concentration used by many laboratories. Twenty percent polymethacrylate was required to achieve the same hybridization rate as 10% dextran sulfate (FIG. 2). Polyacrylate (90,000 molecular weight) was most effective at the low concentration of 1.5% (FIG. 3).

Polyacrylate with 300,000 and 450,000 average molecular weights gave virtually the same results as the 90,000 molecular weight polymer.

A solution of 1,000,000 molecular weight polyacrylate was too viscous to handle and since the 90,000 size was the least viscous, it was chosen for further work.

B. Comparison of DNA Hybridization Rates in the Presence of Polymers

The progress of DNA hybridization reactions in the presence of no polymer, 10% dextran sulfate, 1.5% polyacrylate and 20% polymethacrylate was measured for 24 hours. Each nitrocellulose filter contained 5 ng of immobilized Hind III digested λ DNA and was hybridized with 0.1 μg of $^{35}$S-DNA (4.5×10$^6$ cpm/μg).

Figure 4:
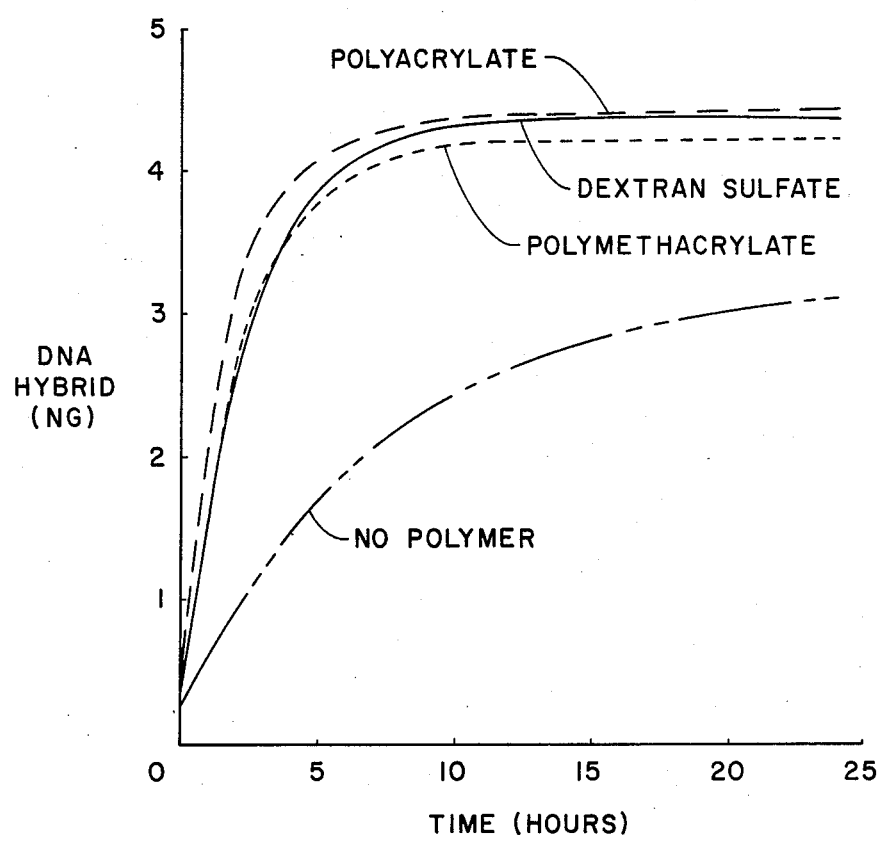
FIG. 4 is a graph showing a comparison of the rates of hybridization in the presence of optimal polymer concentrations.

The data were fitted to a first order kinetic model by a nonlinear regression method described by Duggleby (1981), Anal. Biochem. 110:9-18. The experimental points fit the curves calculated for first order reactions (FIG. 4). The rate constants used to calculate the curves are presented in Table 1. The rates measured with the polymers did not differ substantially, but they were about three times faster than the rate measured in the absence of polymer.

TABLE 1

| Hybridization Rate Constants | |
|---|---|
| Condition | Rate Constant (Hr$^{-1}$) |
| No Polymer | 0.14 |
| 10% Dextran Sulfate | 0.45 |
| 1.5% Polyacrylate | 0.56 |
| 20% Polymethacrylate | 0.49 |

C. Nonspecific Binding of Probe to Nitrocellulose Membrane

Figure 5:
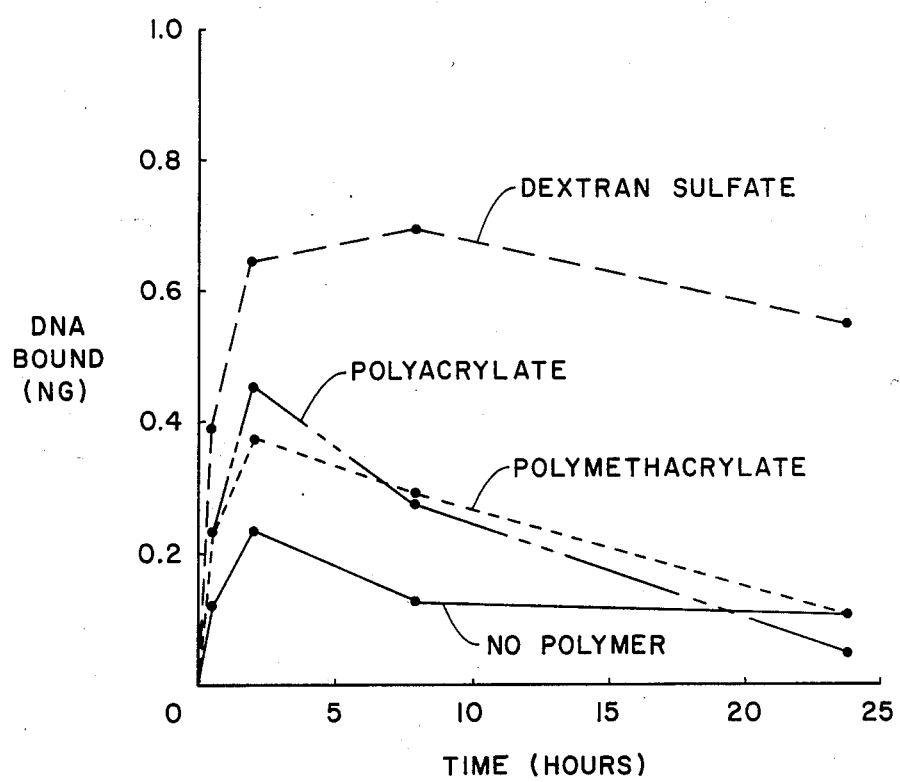
FIG. 5 is a graph showing the effect of the polymers on nonspecific binding of DNA to a nitrocellulose support.

Nonspecific binding of the $^{35}$S-DNA probe to nitrocellulose membrane was increased about four-fold by 10% dextran sulfate (FIG. 5). Each nitrocellulose filter contained 5 μg of immobilized salmon sperm DNA and was subjected to prehybridization treatment and then incubated with 0.1 μg of $^{35}$S labeled Hind III digest of λ DNA (4.5×10$^6$ cpm/μg) under the hybridization conditions. During early stages of the incubation nonspecific binding in the presence of 1.5% polyacrylate or 20% polymethacrylate was twice that for the control without polymer but by 24 hours the values were nearly the same.

D. Effects of Polymers on Hybridization Rates as a Function of Immobilized DNA Level The amount of $^{35}$S-DNA hybridized to various levels of Hind III digested λ DNA immobilized on the filters was measured after 4.5 hours reaction in the presence of no polymer, 1.5% polyacrylate and 10% dextran sulfate. Each filter contained the indicated quantity of immobilized Hind III digested λ DNA and was hybridized for 4.5 hours with 100 ng of $^{35}$S-DNA (specific activity 16.7×10$^6$ cpm/μg). As shown in Table 2, the enhancement of hybridization by both polymers decreased as the DNA level on the filter increased, and at 1 μg DNA the polymers were ineffective. The failure of the polymers to accelerate hybridization at high levels of immobilized DNA can be attributed to faster self-annealing of the probe in the presence of polymers, thus reducing the availability of single stranded probe for hybridization with DNA on the filter.

TABLE 2
Relationship Between Enhancement of Hybridization by Polymers and the Level of Immobilized DNA

| Immobilized DNA ng/Filter | DNA Hybrid (ng) in the Presence of | | |
|---|---|---|---|
| | No Polymer | 10% Dextran Sulfate | 1.5% Polyacrylate |
| 2 | 0.7 | 1.9 | 1.7 |
| 10 | 2.5 | 4.7 | 4.5 |
| 100 | 14.9 | 11.8 | 12.5 |

Discussion

The anionic polymers, dextran sulfate, polyacrylate and polymethacrylate, accelerated the hybridization of soluble DNA with complementary DNA immobilized on nitrocellulose. The acceleration was virtually the same when optimal concentrations of the polymers were employed (FIG. 4). These concentrations were 1.5% polyacrylate, 20% polymethacrylate and 10% dextran sulfate. Since polyacrylate is the least expensive polymer and is effective at a lower concentration, it is a particularly attractive substitute for dextran sulfate in hybridization reactions.

Polyacrylate and polymethacrylate have the additional advantage that nonspecific binding of the DNA probe to the nitrocellulose membrane is lower as compared to the results obtained with dextran sulfate (FIG. 5). Nonspecific binding in the presence of dextran sulfate has been a problem with both cellulose and nitrocellulose supports as reported by Wetmur, supra, and Ranki et al, supra. With polyacrylate and polymethacrylate nonspecific binding increases initially and then declines to the level measured without polymers (FIG. 5). Under the same conditions, dextran sulfate gives a higher level of nonspecific binding which remains nearly constant at long incubation times.

The polymers enhanced the hybridization of DNA more effectively when low levels of DNA were immobilized on the nitrocellulose membrane (Table 2). This is a fortuitous situation which allows improved detection of very low levels of specific DNA sequences. Polymethacrylate and particularly polyacrylate have advantages over the prior art compound dextran sulfate as accelerators of nucleic acid hybridization.

Obviously, many modifications and variations of the invention as hereinbefore set forth can be made without departing from the spirt and scope thereof.

What is claimed is:

1. A method for increasing the rate of hybridization between two complementary polynucleotide segments in an aqueous medium, comprising the step of:
   forming an aqueous medium containing said complementary polynucleotide segments and polyacrylate or polymethacrylate having a molecular weight between about 5,000 and 1,000,000 daltons, the polyacrylate or polymethacrylate being present in the aqueous medium at a concentration effecitve to produce an observable increase in the rate of hybridization.

2. The method of claim 1 wherein the polyacrylate is a polyacrylate salt that is added to the aqueous medium.

3. The method of claim 2 wherein an amount of polyacrylate salt is added to the aqueous medium to produce a solution of polyacrylate at a concentration between about 0.2 and about 10 percent (w/v).

4. The method of claim 3 wherein the concentration of polyacrylate is about 1.5 percent (w/v).

5. The method of claim 1 wherein the polymethacrylate is a polymethacrylate salt that is added to the aqueous medium.

6. The method of claim 5 wherein an amount of polymethacrylate salt is added to the aqueous medium to produce a solution of polymethacrylate at a concentration between about 1.0 and 50 percent (w/v).

7. The method of claim 6 wherein the concentration of polymethacrylate is about 20 percent (w/v).

8. The method of claim 1 wherein the polyacrylate or polymethacrylate has a molecular weight between about 50,000 and about 500,000 daltons.

9. In a method for determining a particular polynicleotide sequence in a test sample comprising single stranded nucleic acids, comprising the steps of (a) forming an aqueous assay medium comprising the sample nucleic acids and a polynucleotide probe having a base sequence substantially complementary to the sequence to be determined, and (b) determining the formation of hydridized probe,
   the improvement which comprises including polyacrylate or polymethacrylate having a molecular weight between about 5,000 and 1,000,000 daltons in the aqueous medium at a concentration effective to produce an observable increase in the rate of hybridization between the sequence to be determined and the probe sequence.

10. The method of claim 9 wherein the single stranded sample nucleic acids are immobilized prior to formation of the assay medium with the probe.

11. The method of claim 10 wherein the sample nucleic acids are immobilized by adsorption to nitrocellulose.

12. The method of claim 10 wherein the probe is labeled.

13. The method of claim 9 wherein the probe is immobilized.

14. The method of claim 9 wherein both the sample nucleic acids and the probe are in solution in the assay medium.

15. The method of claim 9 wherein the polyacrylate is a polyacrylate salt that is added to the aqueous medium.

16. The method of claim 15 wherein an amount of polyacrylate salt is added to the aqueous medium to produce a solution of polyacrylate at a concentration between about 0.2 and 10 percent (w/v).

17. The method of claim 16 wherein the concentration of polyacrylate is about 1.5 percent (w/v).

18. The method of claim 15 wherein the polyacrylate has a molecular weight between about 50,000 and about 500,000 daltons.

19. A reagent system for determining a particular polynucleotide segment in a test sample, comprising in the same or different containers in a packaged combination,
  (1) a polynucleotide probe having a base sequence substantially complementary to the sequence to be determined, and
  (2) an amount of polyacrylate or polymethacrylate having a molecular weight between about 5,000 and 1,000,000 daltons effective to produce an observable increase in the rate of hybridization between said probe and the sequence to be determined in an aqueous medium.

20. The reagent system of claim 19 comprising the probe and a polyacrylate salt.

21. The reagent system of claim 19 comprising the probe and a polymethacrylate salt.

22. The reagent system of claim 19 wherein the polyacrylate or polymethacrylate salt has a molecular weight between about 50,000 and about 500,000 daltons.

23. The reagent system of claim 19 which additionally comprises a solid support capable of immobilizing single stranded nucleic acids in the test sample.

24. The reagent system of claim 23 wherein the solid support is nitrocellulose.

25. The reagent system of claim 23 wherein the probe is labeled.

26. The reagent system of claim 19 wherein the probe is immobilized.

27. The method of claim 1 wherein both of the complementary polynucleotide segments are in solution in the aqueous medium.

28. The method of claim 1 wherein one of the two complementary polynucleotide segments is immobilized.

* * * * *